United States Patent [19]
Shelton et al.

[11] Patent Number: 5,312,453
[45] Date of Patent: May 17, 1994

[54] RATE RESPONSIVE CARDIAC PACEMAKER AND METHOD FOR WORK-MODULATING PACING RATE DECELERATION

[75] Inventors: Michael B. Shelton, Minneapolis; William J. Combs, Eden Prairie; Tommy D. Bennett, Shoreview; Michael R. Tollinger, Andover; Kenneth M. Riff, Plymouth, all of Minn.

[73] Assignee: Medtronic, Inc., Minneapolis, Minn.

[21] Appl. No.: 880,877

[22] Filed: May 11, 1992

[51] Int. Cl.$^5$ ............................................. A61N 1/00
[52] U.S. Cl. ........................................................ 607/19
[58] Field of Search .............. 128/419 PG; 607/19–26

[56] References Cited

U.S. PATENT DOCUMENTS

| | | | |
|---|---|---|---|
| 4,379,459 | 4/1983 | Stein | 128/419 |
| 4,476,868 | 10/1984 | Thompson | 128/419 |
| 4,485,813 | 12/1984 | Anderson et al. | 128/675 |
| 4,556,063 | 12/1985 | Thompson et al. | 128/419 |
| 4,719,920 | 1/1988 | Alt et al. | 128/419 |
| 4,722,342 | 2/1988 | Amundson | 128/419 |
| 4,770,177 | 9/1988 | Schroeppel | 128/419 PG |
| 4,901,726 | 2/1990 | Hansen | 128/419 PG |
| 5,052,388 | 10/1991 | Sivula et al. | 128/419 |
| 5,076,271 | 12/1991 | Lekholm et al. | 128/419 PG |
| 5,101,824 | 4/1992 | Lekholm | 128/419 PG |
| 5,127,404 | 7/1992 | Wyborny et al. | 128/419 |
| 5,134,997 | 8/1992 | Bennett et al. | 128/419 |

FOREIGN PATENT DOCUMENTS 0256617 2/1988 European Pat. Off. .
0310025 4/1989 European Pat. Off. .

*Primary Examiner*—Lee S. Cohen
*Assistant Examiner*—Marianne Parker
*Attorney, Agent, or Firm*—Reed A. Duthler; Harold R. Patton

[57] ABSTRACT

A rate-responsive cardiac pacemaker in which deceleration of the pacing rate is modulated according to recent patient activity or "work". Based on signals provided from an activity sensor in the pacemaker, the pacemaker maintains and periodically recomputes a work value corresponding to the amount of patient activity detected over time. In response to a decrease in or cessation of detected patient activity, the pacemaker reduces the pacing rate, first at a more rapid deceleration rate, then at a lower deceleration rate, and then once again at a more rapid deceleration rate. The length of time during which the pacing rate is reduced at the lower deceleration rate is modulated according to the work value maintained by the pacemaker. The work-modulated pacing rate deceleration occurs only if certain achievement criteria are met, the achievement criteria being specified in terms of the amount of time the pacemaker's target pacing rate exceeds a predetermines rest value, and the difference between the target rate and the rest rate.

5 Claims, 9 Drawing Sheets

RATE RESPONSIVE CARDIAC PACEMAKER AND METHOD FOR WORK-MODULATING PACING RATE DECELERATION

FIELD OF THE INVENTION

This invention relates to the field of implantable medical devices, and more particularly relates to pacemakers which respond to a patient's metabolic demand and varies the decay rates of the pacing rate in substantial similarity to the heart's normal behavior.

BACKGROUND OF THE INVENTION

Early cardiac pacemakers provided a fixed-rate stimulation pulse generator that could be reset, on demand, by sensed atrial and/or ventricular depolarizations. Modern pacemakers include complex stimulation pulse generators, sense amplifiers, and leads which can be configured or programmed to operate in single- or dual-chamber modes of operation, delivering pacing stimuli to the atrium and/or ventricle at fixed rates or rates that vary between an upper rate limit and a lower rate limit.

In recent years, single- and dual-chamber pacemakers have been developed which measure parameters which are directly or indirectly related to the patient's metabolic requirements (i.e., demand for oxygenated blood) and vary the pacing rate in response to such parameters. Such measured parameters include, for example, physical activity of the patient, right ventricular blood temperature, venous blood oxygen saturation, respiration, minute ventilation, and various pre-and post-systolic time intervals measured by impedance or pressure sensors within the right ventricle of the heart. Such sensor-driven pacemakers have been developed for the purpose of restoring rate response to exercise in patients lacking the ability to increase rate adequately by exertion.

In general, a rate-responsive pacemaker includes a sensor which produces an output that varies between a maximum sensor output level and a minimum sensor output level ("sensor output"). The pacemaker delivers pacing stimuli at a pacing rate ("pacing rate") which varies as a linear or monotonic function ("f") of the sensor output, between a selectable lower pacing rate ("lower rate limit") and upper pacing rate ("upper rate limit"). Function f has a selectable slope, where the slope of f corresponds to the ratio of pacing rate change to sensor output change. That is, the slope of f reflects the amount of change—increase or decrease—in the pacing rate resulting from an incremental change in sensor output. The slope of f is adjustable by means of an external programmer along with the lower and upper rate limit values. Thus, the pacing rate typically provided is equal to the programmed lower rate limit plus an increment which is a function of the measured sensor output, as follows:

pacing rate = lower rate + f(sensor output).

While this rate response technique provides a useful and workable system between programmed parameters, the behavior of the pacemaker is complex and often not readily apprehensible. Pacemakers that measure the physical activity of the patient by means of a piezoelectric transducer have become popular among rate-responsive pacemakers. Such a rate-responsive pacemaker employing a piezoelectric transducer is disclosed in U.S. Pat. No. 4,485,813 to Anderson et al. and assigned to the assignee of the present invention, which patent is incorporated herein by reference in its entirety.

Some temperature-sensing pacemakers have employed relatively more complex functions to take into account an initial dip in temperature due to the onset of exercise. One such pacemaker is described in U.S. Pat. No. 4,719,920 to Alt et al.

Furthermore, the decay slope of conventional activity-based rate-responsive pacemakers do not approximate the heart's normal behavior, in that they are programmed to follow a curve based on a single time constant. This discrepancy between the normal heart deceleration function at the end of physiologic stresses due to accumulated metabolic debt, and the conventional pacemaker decay function has not been rectified by any pacemaker presently available on the market and known to the inventors.

Thus, the inventors believe that it would be desirable to provide a cardiac pacemaker of the rate-responsive type which varies its attack and/or decay pacing rates in harmony with the heart's normal behavior.

In U.S. Pat. No. 5,134,997 filed Aug. 14, 1990, by Bennett et al. entitled "Rate Responsive Pacemaker and Pacing Method" (hereinafter referred to as the Bennett et al. reference) there is disclosed a rate-responsive pacemaker having a modified pacing rate decay curve after a period of increased activity. The method disclosed in the Bennett et al. reference includes the steps of selecting a set of predetermined achievement criteria such as an achievement rate and an achievement duration or time interval. The achievement rate is initially selected between an upper pacing rate and a first pacing rate switch threshold. The pacing method then determines whether the achievement criteria have been met. If the achievement criteria have been met, then the decay time constant of the pacing rate decay curve changes from a first value to a second value when the pacing rate drops below the first pacing rate switch threshold.

Further in accordance with the Bennett et al. reference, a second pacing rate switch threshold lower than the first pacing rate switch threshold is selected, and if the achievement criteria have been met, then the pacing rate decay time constant is modified from the second value to a third value when the pacing rate drops below the second pacing rate switch threshold. This third value of the pacing rate decay time constant may be equal to the first value.

According to Bennett et al., the decay rate time constant is not modified in the above-described manner if the achievement criteria have not first been satisfied.

The Bennett et al. pacemaker also periodically calculates a new activity pacing rate, and calculates a new activity target rate based upon the activity sensor output. The achievement rate is calculated as follows:

Achievement Rate = Lower Rate + A(Upper Rate − Lower Rate)

where "A" is a percentile value. Thus, if the programmed upper and lower rate settings define a range of possible pacing values, the achievement rate is defined as some percentage of that range. Similarly, the first pacing rate switch threshold is calculated as:

First Pacing Rate Switch Threshold = Lower Rate + U(Upper Rate − Lower Rate)

where "U" is a percentile value. The second pacing rate switch threshold is defined as:

Second Pacing Rate Switch Threshold=Lower Rate+10% of Lower Rate.

The Bennett et al. reference is hereby incorporated herein by reference in its entirety. As would be apparent to one of ordinary skill in the pacing art, the modified pacing rate decay curve disclosed by Bennett et al. comprises first and third decay phases defined by the programmed decay rate time constant, and a second decay phase, interposed between the first and third phases, in which the programmed decay rate time constant is temporarily replaced with a modified time constant. The boundary points between the first and second decay phases, and the second and third decay phases, are defined in terms of pacing rate. The transition from the first phase to the second phase occurs at a point where the pacing rate drops to the first pacing rate switch threshold, and the transition from the second phase to the third phase occurs at a point where the pacing rate drops to the second pacing rate switch threshold. Although the first and second pacing rate switch thresholds may be programmable values, the decay rate will only change at these programmed values. Moreover, while the programmed and modified time constants are programmable value, the pacing rate decay will occur at one or the other of these programmed values unless the decay parameters are re-programmed. Thus, the Bennett et al. pacemaker could be generally characterized as modifying decay curve by changing the time constant of the pacing rate decay, assuming the achievement criteria have been reached, during an interval determined by the current pacing rate.

By way of comparison, a pacemaker in accordance with one embodiment of the present invention can be generally characterized as modifying the decay curve by changing the time constant of the pacing rate decay, assuming the achievement criteria have been reached, during an interval determined not by the current pacing rate, but by a measure of the amount of work recently performed by the patient.

It is believed by the inventors that it would be advantageous to provide a pacemaker in which the decay time constant is modified based not strictly upon the current pacing rate, but also upon a measure of the patient's recent levels of exertion, the pacemaker will more effectively mimic the deceleration behavior of a healthy heart.

SUMMARY OF THE INVENTION

Accordingly, the present invention provides a rate-responsive pacemaker in which the decay or deceleration of the pacing rate in response to decreases in detected patient activity is controlled according to a metric of recent work performed by the patient.

Specifically, a pacemaker in accordance with the present invention maintains a numeric "Work" value that is periodically recomputed in conjunction with periodic calculations of a rate-responsive Target Rate. When detected patient activity is such that the rate-responsive Target Rate exceeds the pacing rate, the pacing rate is in a state of acceleration and the Work value is periodically increased by a varying incremental amount proportional to the difference between the Target Rate and the pacing rate. A "ceiling" or upper limit on the Work value may be imposed.

When patient activity decreases or ceases, the rate-responsive Target Rate will also decrease. When the Target Rate is below the current pacing rate, the pacing rate is in a state of deceleration. In this case, the Work value is periodically and incrementally decreased by an incremental amount referred to as the Work Decay value. In the preferred embodiment, recomputation of the Target Rate and Work value occurs periodically, for example every two seconds.

The deceleration of the pacing rate occurs in several distinct phases. In the case that the decelerating pacing rate exceeds a preselected Switch Rate, below the programmed Upper Rate Limit, a first, Initial Deceleration Phase occurs in which the pacing deceleration rate is governed by a first, shorter time constant. The Initial Deceleration Phase continues until the pacing rate reaches the Switch Rate. When a decelerating pacing rate is less than or equal to the Switch Rate, a intermediate, Work-Modulated Deceleration Phase occurs, in which the pacing deceleration rate is governed by a second, longer time constant. The duration of the Work-Modulated Deceleration Phase is determined according to the Work value during that phase. By definition, the Target Rate will be less than the pacing rate during the Work-Modulated Deceleration Phase, so that during this phase the Work value will itself be decaying. The end of the Work-Modulated Deceleration Phase occurs when the Work value has decayed to zero.

After the Work-Modulated Deceleration Phase, a final, Latent Deceleration Phase brings the pacing rate down to the programmed Lower Rate Limit. During the Latent Deceleration Phase, the pacing rate deceleration is governed by a shorter time constant than during the Work-Modulated Phase. The Latent Deceleration Phase time constant may or may not be the same as the time constant for the Initial Deceleration Phase.

In a preferred embodiment of the invention, a Work-Modulated Deceleration Phase will only occur after certain Achievement Criteria have been reached. The Achievement Criteria are expressed in terms of a range of Achievement Durations and a range of Achievement Times. Only when the Target Rate has been greater than a predetermined rest rate for a sufficient time to satisfy the Achievement Criteria will Work-Modulated pacing rate deceleration occur. Once the pacing rate decelerates to the programmed lower rate, the Achievement Criteria must again be fulfilled before Work-Modulated pacing rate deceleration will occur.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
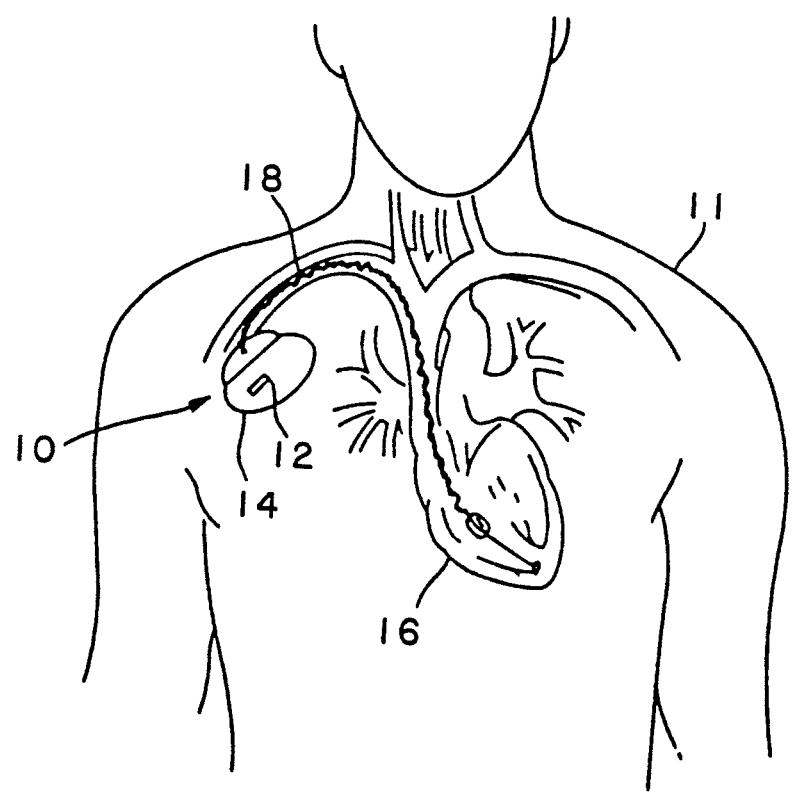
FIG. 1 is an illustration showing placement of a pacemaker in accordance with the disclosed embodiment of the invention in a patient.

Referring to FIG. 1, there is illustrated the placement of a pacemaker 10 in accordance with one embodiment of the present invention. Pacemaker 10 is shown in FIG. 1 as it would be implanted in a patient 11. The preferred embodiment of the invention includes at least one activity sensor 12, which may be, for example, a piezoelectric element disposed on a can or housing 14 of a pacemaker 10. Pacemaker 10 may additionally include other sensors, such as a pressure sensor or the like implanted within heart 16 or disposed on the distal end of pacemaker lead 18. A pacemaker which measures the physical activity of a patient by means of a piezoelectric transducer is disclosed in the above-referenced U.S. Pat. No. 4,485,813 to Anderson et al. It is to be understood that the present invention is not limited in scope to either single-sensor or dual-sensor pacemakers, and that other sensors besides activity and pressure sensors could be used in practicing the present invention. Nor is the present invention limited in its scope to single-chamber pacemakers. A multiple-chamber (e.g., dual-chamber) pacemaker can also be used in practicing the present invention. It should also be understood that while the present invention will be described herein with reference to the decay curve of the pacemaker's pacing rate in the context of an activity-based rate-responsive pacemaker, the inventive concept herein can be implemented for modifying the attack curve of the pacing rate, and may be employed in pacemakers using pressure and/or other types of sensors.

It is believed that a description of prior art rate-responsive pacemakers, and in particular, the pacemaker described in the Bennett et al. reference will facilitate a better understanding of a pacemaker in accordance with the present invention.

Figure 2:
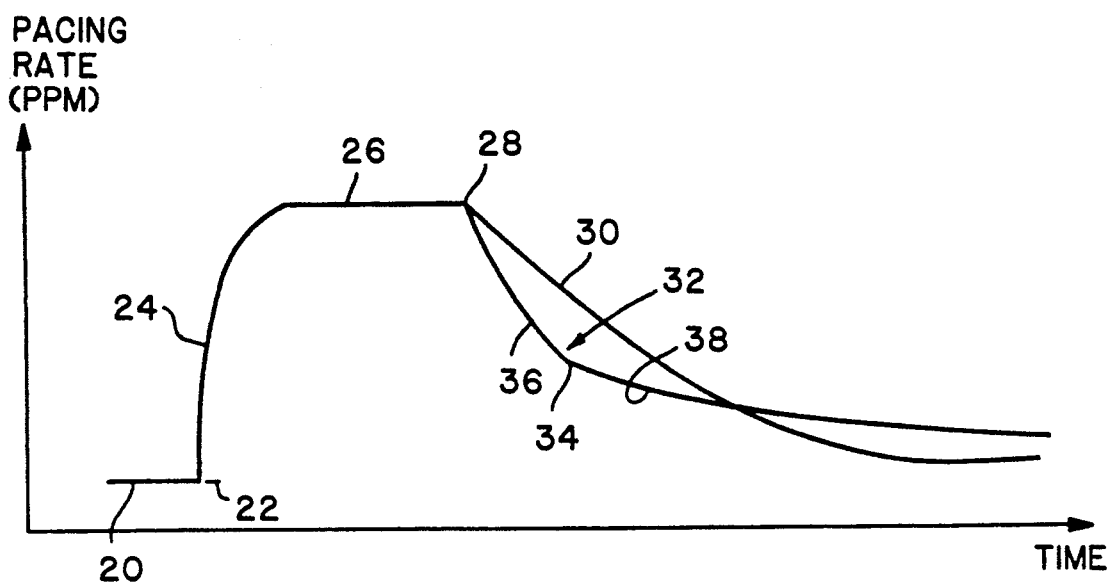
FIG. 2 is a graph of pacing rate versus time showing a prior-art pacemaker's pacing rate response following cessation of patient activity, compared to a normal heart's response thereto.

In FIG. 2, a representative pacing rate curve for a conventional activity-sensing rate-responsive pacemaker is shown in comparison with a normal heart rate decay curve. In FIG. 2, the vertical axis represents the pacing rate in pulses per minute (PPM), and the horizontal axis represents time.

In FIG. 2, the patient is initially at rest, and thus no activity is sensed. During this period of rest, pacemaker 10 delivers pacing pulses at its programmed base or lower rate (LR), as indicated by the line 20. When the patient begins exercising so that activity sensor 12 begins detecting activity, the pacing rate begins to increase, beginning at deflection point 22. The attack or acceleration curve 24 shows the pacemaker responding to such increased levels of detected activity.

When attack curve 24 reaches a plateau 26, the pacing rate generally stabilizes at an activity-determined rate or an upper rate for the duration of the exercise or physical activity. A deflection point 28 corresponds in time to the cessation or substantial reduction in the patient's activity level. The pacing rate is said to be decelerating beginning at point 28.

Two decay or deceleration curves 30 and 32 descend from deflection point 28 and indicate a decrease in the patient's detected activity level. In the absence of intervening instances of heightened activity, curves 30 and 32 tend to approach a predetermined lower pacing rate.

Decay curve 30 represents the deceleration curve in a conventional pacemaker, as exemplified in U.S. Pat. No. 4,722,342 to Amundson. The decay curve 32, on the other hand, represents the heart's normal deceleration rate, as illustrated in a textbook by Myrvin H. Ellestad, M.D., entitled "Stress Testing Principles and Practice", pages 489-492.

It is apparent that deceleration curves 30 and 32 do not match completely, in that conventional pacemakers pace at an elevated rate, i.e., curve 30, with respect to the typical human response, i.e., curve 36, and thereafter return to the resting or lower rate sooner than the typical human response 38. This elevated pacing rate in conventional pacemakers may cause a sensation of the heart rate "racing" or beating too fast at the end of activity, perhaps even provoking undesirable side-effects. Additionally, conventional pacemakers may pace too slowly for several minutes after the end of activity.

Curve 32 in FIG. 2 comprises two decay portions, an initial portion 36 and a latent portion 38, each having a different decay time constant. As will be hereinafter explained in more detail, the selection of switch point 34 and the time constants of the initial and latent decay portions 36 and 38 are important subjects of the Bennett et al. invention.

DEFINITIONS OF TERMS

The following definitions of terms used herein will assist in a better understanding of the present invention:

Achievement Criteria

Values supplied by the clinician which set an attainment threshold for the pacing rate. This threshold comprises a rate component (Achievement Rate) and a time component (Achievement Duration). Achievement Rate is a programmable percentage of the difference between the programmed Lower Rate (LR) and the programmed Upper Rate (UR). Achievement Duration is a minimum time interval over which the rate-responsive target pacing rate must exceed the Achievement Rate. In the Bennett et al. patent, the Achievement Rate is specified by the clinician as an absolute pacing rate in the range from 70-PPM to 175-PPM in 1-PPM intervals, and the Achievement Duration is fixed at four seconds. An alternative embodiment in Bennett allowed the criterion to be a percentage of the programmed upper rate. In accordance with the presently disclosed embodiment of the invention, however, the Achievement Criteria are expressed in a normalized form, so that various combinations of pacing rates and durations will satisfy the Achievement Criteria. Moreover, the normalized expression of the Achievement Criteria allows the deceleration response in accordance with the present invention to be realized for any allowable combination of programmed UR and LR values. This normalization will be hereinafter described in greater detail with reference to FIG. 6.

Activity Count

Activity Count is a measure of the output of the activity sensor over a predetermined interval of time. In the presently disclosed embodiment of the invention, each event during a two-second period in which the amplitude of the sensor output exceeds a predetermined activity threshold is counted and retained. The Activity Count is updated every two seconds, and its aggregate value comprising the count value accumulated at the end of two two-second cycles (i.e., after four seconds) is used in the calculation of the sensor Target Pacing rate for activity. A pacemaker employing a piezoelectric signal and maintaining the two-second activity count as just described is disclosed in pending U.S. Pat. No. 5,052,388 to Sivula et al. entitled "Method and Apparatus for Implementing Activity Sensing in a Pulse Generator", which reference is hereby incorporated by reference in its entirety.

Activity Rate Response Gain

This setting corresponds to the slope of the function correlating the activity-based Target Rate to the Activity Count value which corresponds to the activity sensor output. The setting for the Activity Rate Response Gain, sometimes alternatively referred to as the "activity sensor gain", corresponds to a particular rate-response curve (RR). With rate-response, the allowed programmable values for the Activity Rate Response Gain range from 1 to 10 at setting intervals of 1.

Activity Response Time Acceleration Constant

This value restricts the rate at which the activity-based sensor pacing rate can increase, such that an activity "attack" curve provides for a more gradual and physiologically appropriate change in pacing rate. In the presently disclosed embodiment of the invention, these time values represent the time required to reach 90% of the difference between a first steady-state activity-driven pacing period (i.e., constant activity signal for at least a six-second interval) and a second, shorter, steady-state, activity driven pacing period when a step increase in activity occurs. With rate-response, the allowed programmable values for the Activity Response Time Acceleration Constant are 0.25-minutes, 0.5-minutes, and 1.2-minutes.

Activity Response Time Deceleration Constant

This value restricts the rate at which the activity-based sensor Pacing Rate can decrease, such that an activity "decay" curve provides for a more gradual and physiologically appropriate change in pacing rate. In the presently disclosed embodiment of the invention, the Activity Response Time Deceleration Constant represents the time required to reach 90% of the difference between a first steady-state activity-driven pacing period (constant activity signal input for at least six seconds), and a second, longer, steady-state, activity-driven pacing period when a step decrease in activity level occurs. With rate-response, the allowed programmable values for the Activity Response Time Deceleration Constant are 2.5-minutes, 5-minutes, or 10-minutes.

Activity Threshold

This is a minimum value which the amplitude of the activity sensor output must exceed in order to serve as input to the rate determination algorithm. The higher the threshold, the greater the amplitude necessary to become an event counted in the Activity Count. With rate-response, the allowed programmable values for the Activity Threshold are LOW, MEDIUM LOW, MEDIUM, MEDIUM HIGH, and HIGH.

Lower Rate (LR)

This is a value supplied by the clinician which establishes a lower limit on the pacing rate. If the sensor is disabled, or its sensor output is not high enough to register an activity count that would increase the rate, the pacemaker will deliver stimulating pulses at the programmed Lower Rate. Allowed programmable parameter values for Lower Rate may range from 30-to 180-PPM in 5-PPM intervals.

Upper Rate (UR)

The Upper Rate is a value supplied by the clinician which limits the maximum stimulation rate in rate-responsive mode, such that the sensor-driven pacing rate does not become hemodynamically excessive. Allowed programmable values for the Upper Rate range from 30-PPM to 180-PPM at 5-PPM intervals, provided that UR must always be greater than or equal to the programmed LR.

Pacing Rate

This value is calculated by pacemaker 10 in conjunction with the activity sensor, based upon its respective Target Rate and the contribution thereto based upon its respective acceleration and deceleration function. That is, the actual pacing rate may at any time differ from the activity-based Target Rate if the pacing rate is prevented from immediately increasing or decreasing to the Target Rate due to the limitations imposed by the Acceleration and Deceleration functions described herein.

Target Rate

The Target Rate is calculated by pacemaker 10 in conjunction with the activity sensor, based upon programmed settings and the respective sensor output.

Figure 3:
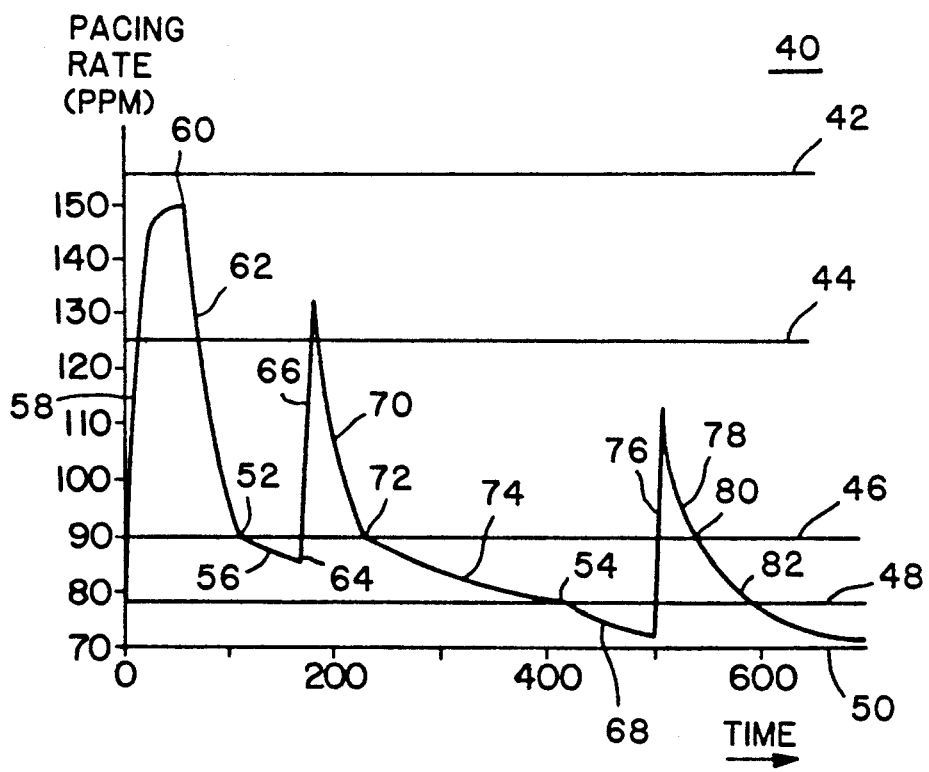
FIG. 3 is a graph of pacing rate versus time showing a prior-art pacemaker's pacing rate response to several episodes of patient activity.

Operation of the Bennett et al. pacemaker will now be briefly described with reference to FIG. 3. FIG. 3 illustrates an exemplary activity attack and decay curve 40 for the Bennett et al. pacemaker. The vertical axis of FIG. 3 represents the pacing rate in PPM and the horizontal axis represents time in seconds. Five threshold levels are illustrated as horizontal lines 42, 44, 46, 48, and 50. In particular, line 42 represents the programmed UR, line 44 represents the Achievement Rate, line 46 represents an Upper Switch Rate, line 48 represents a Lower Switch Rate, and line 50 represents the programmed LR.

As noted above, the programmed UR 42 is a value supplied by the physician which limits the maximum stimulation rate when activity reaches or exceeds a predetermined level. Pacemaker 10 is not allowed to pace above UR 42. In the Bennett et al. pacemaker, the Achievement Rate 44 is a value that can be set by the physician representing a predetermined percentage of the difference between UR 42 and LR 50. That is, according to Bennett et al., Achievement Rate is defined as follows:

Achievement Rate = Lower Rate + A(Upper Rate − Lower Rate)

where "A" is a percentile value preferably ranging between 50%-100%. Achievement Rate 44 may vary from one patient to another. However, an exemplary achievement rate disclosed in the Bennett et al. reference is 125-PPM.

The Upper Switch Rate 46 is a value that can be selected by the physician and similarly represents a predetermined percentage of the difference between the programmed LR and UR. In particular, Upper Switch Rate 46 is defined as:

Upper Switch Rate = Lower Rate + U(Upper Rate − Lower Rate)

where "U" is a percentile value. The Upper Switch Rate varies from one patient to another. However, a preferred range of 20%-50% is disclosed in the Bennett et al. reference. The Upper Switch Rate plays an important role in the operation of the Bennett et al. device, in that it determines the location of an upper switch point 52 which is graphically represented in FIG. 3 as the intersection point between activity curve 40 and the line 46 representing the Upper Switch Rate. Upper switch point 52 corresponds to switch point 34 in FIG. 2.

The Lower Switch Rate 48 also plays an important role in the operation of the Bennett et al. device, in that it determines a lower switch point 54, graphically represented in FIG. 3 as the intersection point between activity curve 40 and the line 48 representing the Lower Switch Rate.

The programmed Lower Rate 50 is a value supplied by the physician which limits the minimum stimulation level when activity decreases to, or is, below a certain predetermined LR level. Pacemaker 10 is not allowed to pace below Lower Rate 50. For illustration purposes in the Bennett et al. reference, Lower Rate 50 is chosen as 70-PPM. While the Upper Rate 42, Achievement Rate 44, Upper Switch Rate 46, Lower Switch Rate 48, and Lower Rate 50 can be individually selected, it is to be understood that these values can also be set to nominal default values to simplify programming procedures.

Operation of the Bennett et al. pacemaker as depicted in FIG. 3 begins with the patient in an initial resting condition and the pacemaker pacing at the programmed Lower Rate. When the patient is stressed by exercise, the Bennett et al. pacemaker responds by increasing the pacing rate, as illustrated by attack curve 58, until it reaches a maximum pacing rate or plateau 60, at which time the pacing rate stabilizes for the duration of the stress. The pacing rate 60 may or may not be limited by upper rate 42, depending upon the level of detected activity.

If the patient maintains a heightened exercise level, and the Bennett et al. pacemaker has paced above the Achievement Rate 44 for a predetermined interval of time (e.g., four seconds is disclosed in the Bennett et al. reference), then the Bennett et al. pacemaker automatically triggers a modified decay feature. After the modified decay feature is triggered, when the pacing rate is decreased, it is decreased according to a decay curve 62 which is deflected at the upper and lower switch points such as 52 and 54, as the pacing rate falls first to the Upper Switch Rate 46 and then to the Lower Switch Rate 48, respectively. It is stated in the Bennett et al. reference that the four-second Achievement Duration value substantially minimizes false triggering by artifacts.

With continuing reference to FIG. 3, upon decrease of the activity level the Bennett et al. pacemaker begins reducing its pacing rate, with the reduction initially occurring at the programmed Activity Response Time Deceleration constant, for example, 2.5-minutes. However, once the pacing rate reaches the Upper Switch Rate threshold 46, the decay time constant is increased in order to slow the rate at which the pacing rate is reduced. The Bennett et al. modified decay feature simulates the heart's normal behavior under the circumstances, and causes the Bennett et al. pacemaker to respond optimally to the individual patient's cardiovascular needs.

The modified decay curve 56 generally corresponds to the latent decay portion 38 in FIG. 2. If, prior to reaching the Lower Switch Rate 48, the patient resumes a sudden heightened stress or exercise level, then, as indicated by deflection point 64, the pacing rate increases correspondingly, as indicated by attack curve 66. It should be noted that at this stage, since the modified decay curve 330 has not reached the Lower Switch Rate 48, the modified decay feature of the Bennett et al. pacemaker is still enabled and has not been turned off. The modified decay feature will be disabled (turned off) only after the pacing rate drops below the Lower Switch Rate 48, along curve 68, at which time the modified decay feature will not be re-enabled until the Achievement Criteria have again been met.

Therefore, as the pacing rate decay curve 70 reaches the Upper Switch Rate 46, a corresponding switch point 72 causes a change in the deceleration time constant. In this manner, the pacing rate is allowed to decay along the decay curve 337 at the time constant of 45-seconds, and upon reaching the Upper Switch Point 72, the pacing rate follows the modified decay curve 74.

The decay time constant of modified decay curves 56 and 74 are substantially similar, and their time constants can be selected from a range specified in the Bennett et al. reference between 90- to 180-seconds. As a person of ordinary skill in the art would appreciate, decay curves 56 and 74 can have different time constants, depending upon the desired behavior of the pacemaker.

Since, in FIG. 3, attack curve 66 has reached and exceeded the achievement rate threshold 44, it might be desirable to set the time constant of decay curve 74 at an intermediate value between the decay time constant of decay curve 62 (i.e., 45-seconds) and the modified time constant of decay curve 56. By analogy, the decay time constant of curve 70 could also be selected to differ from the conventional 45-second decay time constant of curve 62.

As curve 74 reaches Lower Switch Rate 48, its decay time constant changes to a faster time constant of curve 68, similar to the conventional 45-second time constant. A different time constant can be selected.

Upon reaching lower switch point 54, the modified decay achievement criteria are met, such that as long as the patient's exercise and stress levels do not cause the pacing rate to reach or exceed Achievement Rate 44 for a predetermined length of time, then the pacing rate is allowed to decay at a nominal 45-second time constant.

This feature is illustrated by attack curve 76 which falls short of reaching Achievement Rate 44. Decay curve 78 is followed, even though the pacing rate decays below Upper Switch Rate 46 and Lower Switch Rate 48. Hence, as illustrated, curve 78 is allowed to decay with a single, uninterrupted time constant, since it is presumed that under such circumstances the patient does not require additional time to recuperate from increased sudden stress. Therefore, no deflection is effected at the intersection points 80 and 82.

It is noted in the Bennett et al. reference that intersection points 80 and 82 can become switch points similar to the upper and lower switch points 72 and 54. In the alternative, curve 78 can decay at a time constant different from that of decay curve 62. It is also noted in the Bennett et al. reference that one or more additional upper and lower switch levels can be defined between Achievement Rate 44 and Upper Switch Rate 46, as well as between Upper Switch Rate 46 and Lower Switch Rate 48, in order to generate a more gradual deflection of the overall decay curve.

Figure 4:
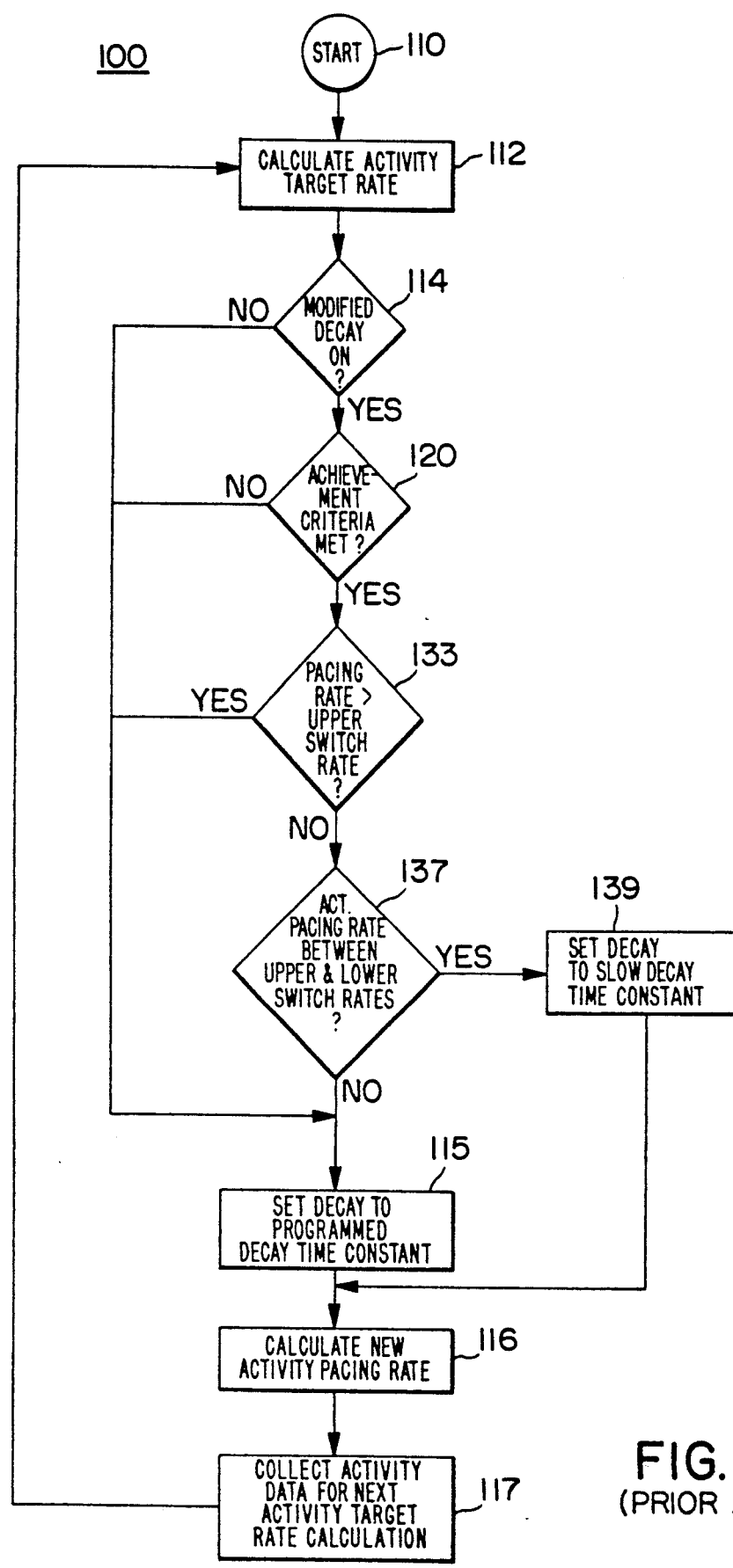
FIG. 4 is a flow diagram depicting the operation of a prior-art rate-responsive pacemaker with a modified pacing decay function.

Turning now to FIG. 4, the operation of the Bennett et al. pacemaker will be described in somewhat greater detail in connection with flow chart 100. The software program and/or hardware starts at 110, and then determines, at 112, a new rate-response Target Rate according to the following equation:

$$TR = \frac{(ActivityCount + D)}{C} \times \left(\frac{32768 \times 60}{328}\right)$$

where TR is the Target Rate as defined above, calculated in response to the activity sensor output; and C and D are programmable values that generate the shape of the rate response curves. The values of C and D are generated by the Bennett et al. pacemaker or by an external programmer (not shown in the Figures) as a function of the selected Upper Rate, Lower Rate, and Rate Response values. C and D are programmed into a memory or storage register of the Bennett et al. pacemaker using conventional programming methods. The Bennett et al. pacemaker includes an arithmetic and logic unit (ALU) capable of making the necessary calculations and controlling the rate of the pacemaker based upon the calculated Target Rate (TR).

An example of a rate-responsive pacemaker in which the target pacing rate is calculated in a manner similar to that of the Bennett et al. reference is the above-referenced Sivula et al. device. Such a pacemaker is also disclosed in pending U.S. patent application Ser. No. 07/794,766 filed on Nov. 15, 1991 in the name of Paul Marc Stein and entitled "Method and Apparatus for Implementing Activity Sensing in a Pulse Generator", which is now incorporated by reference herein in its entirety. While there are numerous well-known pacemakers which calculate a target pacing rate in such a manner as described in the Stein, Sivula et al. and Bennett et al. references, it is to be understood that the present invention is not limited in scope or applicability to only those pacemakers. It is believed by the inventors that the present invention may be effectively and advantageously implemented in various ways in conjunction with various different pacemakers.

Returning to the description of the Bennett et al. pacemaker, each time the physician alters the selected Upper Rate, Lower Rate, or Rate Response settings, the programmer generates a new set of C-term, D-term, switch rate, and achievement rate values, and loads them into memory or program registers in the pacemaker, so that the ALU may calculate the Target Rate thereafter, based upon the updated values. Regardless of which of the selected parameters has changed, the resulting function relating the pacing rate to the sensor output will take the same basic form, extending from the Lower Rate at minimal activity sensor output to the Upper Rate at an achievable sensor output, with a sensor output required to achieve the upper rate decreasing as the rate-response setting is increased.

As indicated in block 112 of FIG. 4, the Bennett et al. pacemaker periodically calculates the activity Target Rate at two-second intervals, along the curve 40 of FIG. 3.

Next, the software determines at 114 whether the modified decay feature in accordance with the Bennett et al. disclosure has been activated or programmably enabled via a programmer such as the Medtronic Model 9760 or the like. If the modified decay feature has not been activated, then the software sets the decay rate to be equal to the programmed decay rate, e.g., 45-second. This is indicated at block 115 in FIG. 4.

The Bennett et al. pacemaker then calculates the next activity pacing rate at 116, and saves the activity related data at 117, for use in calculating the new activity target rate at 112. The above routine is repeated until the modified decay feature is activated.

If the modified decay feature is found to be enabled at block 114, then, as indicated by block 120 the software determines whether the achievement criteria have been met. That is, the software determines whether the pacing rate has been greater than or equal to the Achievement Rate for four seconds or more. If the Achievement Criteria have not been met, then the software, at block 115, sets the decay rate to be equal to the programmed decay rate, calculates the activity pacing rate at 116, saves the activity data at 117, and then calculates the new activity target rate at 412.

If, on the other hand, the Achievement Criteria have been met, then, at block 133, the software determines whether the current pacing rate is greater than the Upper Switch Rate 46. If it is, then, once again, the software sets the decay rate to be equal to the programmed decay rate at block 115, calculates the new activity pacing rate at block 116, saves the activity data at block 117, and calculates the new activity Target Rate at block 412.

If the pacing rate is less than or equal to the Upper Switch Rate 46, then the software determines, at 137, whether the pacing rate is between the Upper Switch Rate 46 and the Lower Switch Rate 48. If it is, then, as indicated by block 439, the software changes the decay rate to the modified or slower decay rate, as illustrated by decay curves 56 and 74 in FIG. 3. The activity pacing rate is then calculated at 116, the activity data is stored at block, 117, and a new activity Target Rate is calculated at block 112.

If the pacing rate is less than the Lower Switch Rate 48, then as indicated by block 115, the software changes the decay rate to the programmed value.

Figure 5:
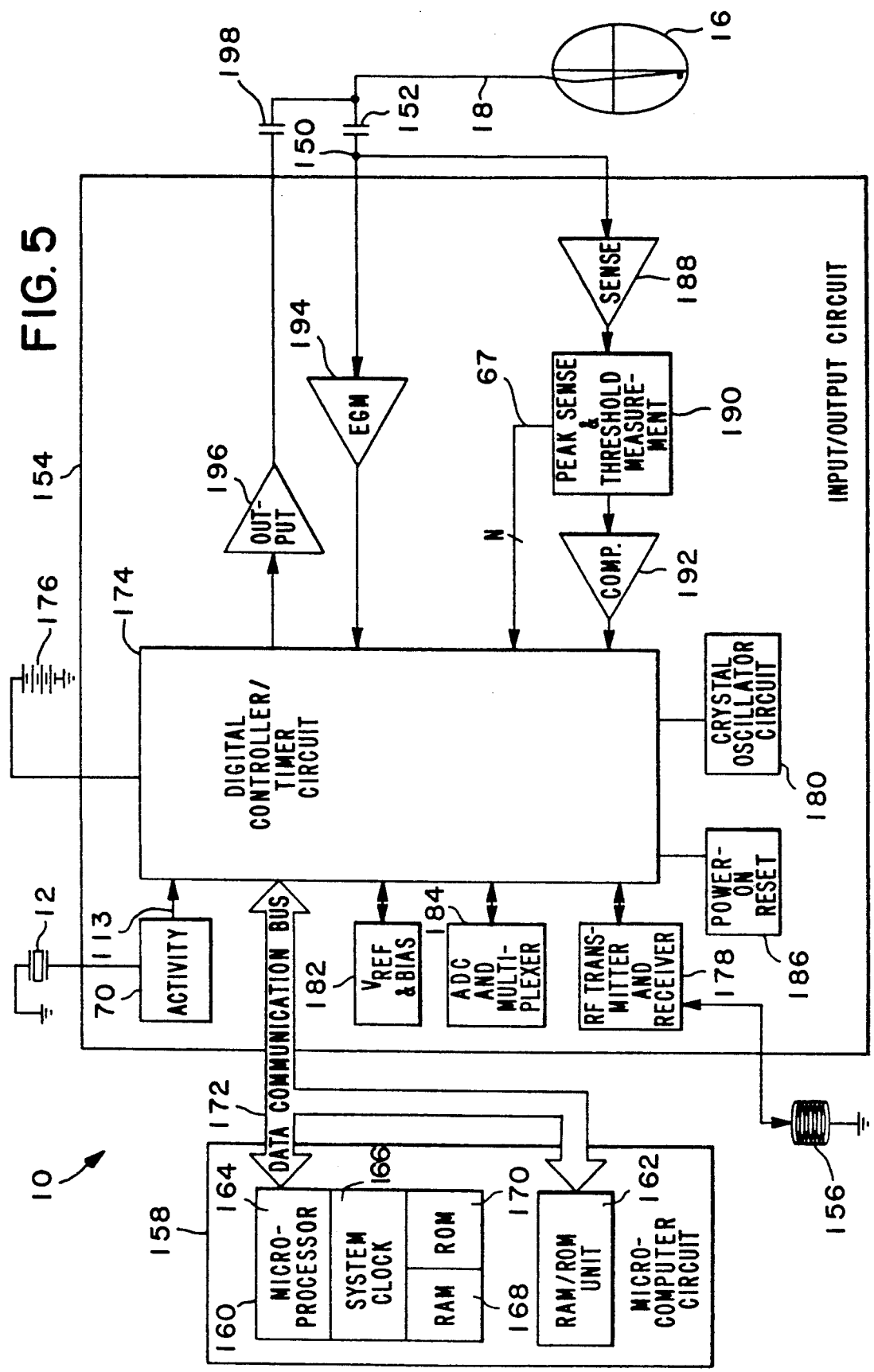
FIG. 5 is a block diagram of a pacemaker in accordance with the disclosed embodiment of the invention.

Turning now to FIG. 5, a block diagram illustrating the constituent components of a pacemaker 10 in accordance with the presently disclosed embodiment of the invention is provided. Although the present invention will be described herein in conjunction with a pacemaker 10 having a microprocessor-based architecture, it will be understood that pacemaker 10 may be implemented in any logic based, custom integrated circuit architecture, if desired. It will also be understood that the present invention may be utilized in conjunction with other implantable medical devices, such as cardioverters, defibrillators, cardiac assist systems, and the like.

In the illustrative embodiment shown in FIG. 5, pacemaker 10 includes an activity sensor 12, which as previously noted may be, for example, a piezoelectric element bonded to the inside of the pacemaker's shield. Such a pacemaker/activity sensor configuration is the subject of the above-referenced patent to Anderson et al., which is hereby incorporated by reference in its entirety. Piezoelectric sensor 12 provides a sensor output which varies as a function of a measured parameter that relates to the metabolic requirements of patient 11.

Pacemaker 10 of FIG. 5 is programmable by means of an external programming unit (not shown in the Figures). One such programmer suitable for the purposes of the present invention is the Medtronic Model 9710 programmer which has been commercially available for several years and is intended to be used with all Medtronic pacemakers. The programmer is a microprocessor device which provides a series of encoded signals to pacemaker 10 by means of a programming head which transmits radio-frequency (RF) encoded signals to pacemaker 10 according to the telemetry system laid out, for example, in U.S. Pat. No. 5,127,404, filed on Sep. 25, 1991 by Wyborny et al., which application is hereby incorporated by reference in its entirety. It is to be understood, however, that the programming methodology disclosed in Wyborny et al. patent is identified herein for the purposes of illustration only, and that any programming methodology may be employed so long as the desired information is transmitted to the pacemaker. It is believed that one of skill in the art would be able to choose from any of a number of available programming techniques to accomplish this task.

The programmer facilitates the selection by a physician of the desired parameter to be programmed and the entry of a particular setting for the desired parameter. For purposes of the present invention, the specifics of operation of the programmer are not believed to be important with the exception that whatever programmer is used must include means for selecting an upper rate (UR), a lower rate (LR), and one of a plurality of rate response (RR) settings to be hereinafter described in greater detail.

In the illustrative embodiment, the lower rate may be programmable, for example from 40 to 90 pulses per minute (PPM) in increments of 10-PPM, the upper rate may be programmable between 100 and 175-PPM in 25-PPM increments, and there may be ten rate response functions, numbered one through ten, available.

In addition, the programmer may include means for selection of acceleration and deceleration parameters which limit the rate of change of the pacing rate. These parameters may be variously referred to in the rate responsive pacemaker context as acceleration and deceleration settings or attack and decay settings. These may be expressed in terms of the time interval required for the pacemaker to change between the current pacing rate and 90% of the desired pacing interval, assuming that the activity level corresponding to the desired pacing rate remains constant. Appropriate selectable values for the programmed acceleration time would be, for example, 0.25 minutes, 0.5 minutes, and 1 minute. Appropriate selectable values for the programmed deceleration time would be, for example, 2.5 minutes, 5 minutes, and 10 minutes.

Pacemaker 10 is schematically shown in FIG. 5 to be electrically coupled via a pacing lead 18 to a patient's heart 16. Lead 18 includes an intracardiac electrode located near its distal end and positioned within the right ventricular (RV) or right atrial (RA) chamber of heart 16. Lead 18 can carry either unipolar or bipolar electrodes as is well known in the art. Although an application of the present invention in the context of a single-chamber pacemaker will be disclosed herein for illustrative purposes, it is to be understood that the present invention is equally applicable in dual-chamber pacemakers.

Lead 18 is coupled to a node 150 in the circuitry of pacemaker 10 through input capacitor 152. In the presently disclosed embodiment, activity sensor 12 is bonded to the inside of the pacemaker's outer protective shield or can 14 (not shown in FIG. 5), as noted with reference to FIG. 1 and in accordance with common practice in the art. As shown in FIG. 5, the output from activity sensor 12 is coupled to an input/output circuit 154.

Input/output circuit 154 contains the analog circuits for interface to heart 16, activity sensor 12, an antenna 156, as well as circuits for the application of stimulating pulses to heart 16 to control its rate as a function thereof under control of the software-implemented algorithms in a microcomputer circuit 158.

Microcomputer circuit 158 comprises an on-board circuit 160 and an off-board circuit 162. On-board circuit 160 includes a microprocessor 164, a system clock circuit 166, and on-board RAM 168 and ROM 170. In the presently disclosed embodiment of the invention, off-board circuit 162 comprises a RAM/ROM unit. On-board circuit 160 and off-board circuit 162 are each coupled by a data communication bus 172 to a digital controller/timer circuit 174. Microcomputer circuit 158 may be fabricated of a custom integrated circuit device augmented by standard RAM/ROM components.

It will be understood that the electrical components represented in FIG. 5 are powered by an appropriate implantable battery power source 176, in accordance with common practice in the art. For the sake of clarity, the coupling of battery power to the various components of pacemaker 10 has not been shown in the Figures.

Antenna 156 is connected to input/output circuit 154 for purposes of uplink/downlink telemetry through RF transmitter and receiver unit 178. Unit 178 may correspond to the telemetry and program logic employed in U.S. Pat. No. 4,556,063 issued to Thompson et al. on Dec. 3, 1985 or in the above-referenced Wyborny et al. patent, both of which are incorporated herein by reference in their entirety. The particular programming and telemetry scheme chosen is not believed to be important for the purposes of the present invention so long as it provides for entry and storage of values of rate-response parameters discussed herein.

A crystal oscillator circuit 180, typically a 32,768-Hz crystal-controlled oscillator, provides main timing clock signals to digital controller/timer circuit 174. A $V_{REF}$ and Bias circuit 182 generates stable voltage reference and bias currents for the analog circuits of input/output circuit 154. An analog-to-digital converter (ADC) and multiplexer unit 184 digitizes analog signals and voltages to provide "real-time" telemetry intracardiac signals and battery end-of-life (EOL) replacement function. A power-on-reset (POR) circuit 186 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 172 to digital controller/timer circuit 174 wherein digital timers and counters are employed to establish the overall escape interval of the pacemaker, as well as various refractory, blanking, and other timing windows for controlling the operation of the peripheral components within input-/output circuit 154.

Digital controller/timer circuit 174 is coupled to sensing circuitry including a sense amplifier 188, a peak sense and threshold measurement unit 190, and a comparator/threshold detector 192. Circuit 174 is further coupled to an electrogram (EGM) amplifier 194 for receiving amplified and processed signals picked up by the electrode disposed on lead 18 which signals are representative of the electrical activity of the patient's heart 16. Sense amplifier 188 amplifies sensed electrical cardiac signals and provides this amplified signal to peak sensed and threshold measurement circuitry 190, which provides an indication of peak sensed voltages and the measured sense amplifier threshold voltage on multiple conductor signal path 67 to digital controller/timer circuit 174. The amplified sense amplifier signal is then provided to comparator/threshold detector 192. Sense amplifier 188 may correspond, for example, to that disclosed in U.S. Pat. No. 4,379,459 issued to Stein on Apr. 12, 1983, incorporated by reference herein in its entirety. The electrogram signal developed by EGM amplifier 194 is used on those occasions when the implanted device is being interrogated by an external programmer, not shown, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference. An output pulse generator 196 provides pacing stimuli to the patient's heart 16 through coupling capacitor 198 in response to a pacing trigger signal developed by digital controller/timer circuit 174 each time the escape interval times out, or an externally transmitted pacing command has been received, or in response to other stored commands as is well known in the pacing art. Output amplifier 196 may correspond generally to the output amplifier disclosed in U.S. Pat. No. 4,476,868 issued to Thompson on Oct. 16, 1984 also incorporated herein by reference in its entirety.

While specific embodiments of input amplifier 188, output amplifier 196, and EGM amplifier 194 have been identified herein, this is done for the purposes of illustration only. It is believed by the inventor that the specific embodiments of such circuits are not critical to the present invention so long as they provide means for generating a stimulating pulse and provide digital controller/timer circuit 174 with signals indicative of natural and/or stimulated contractions of the heart.

Figure 6:
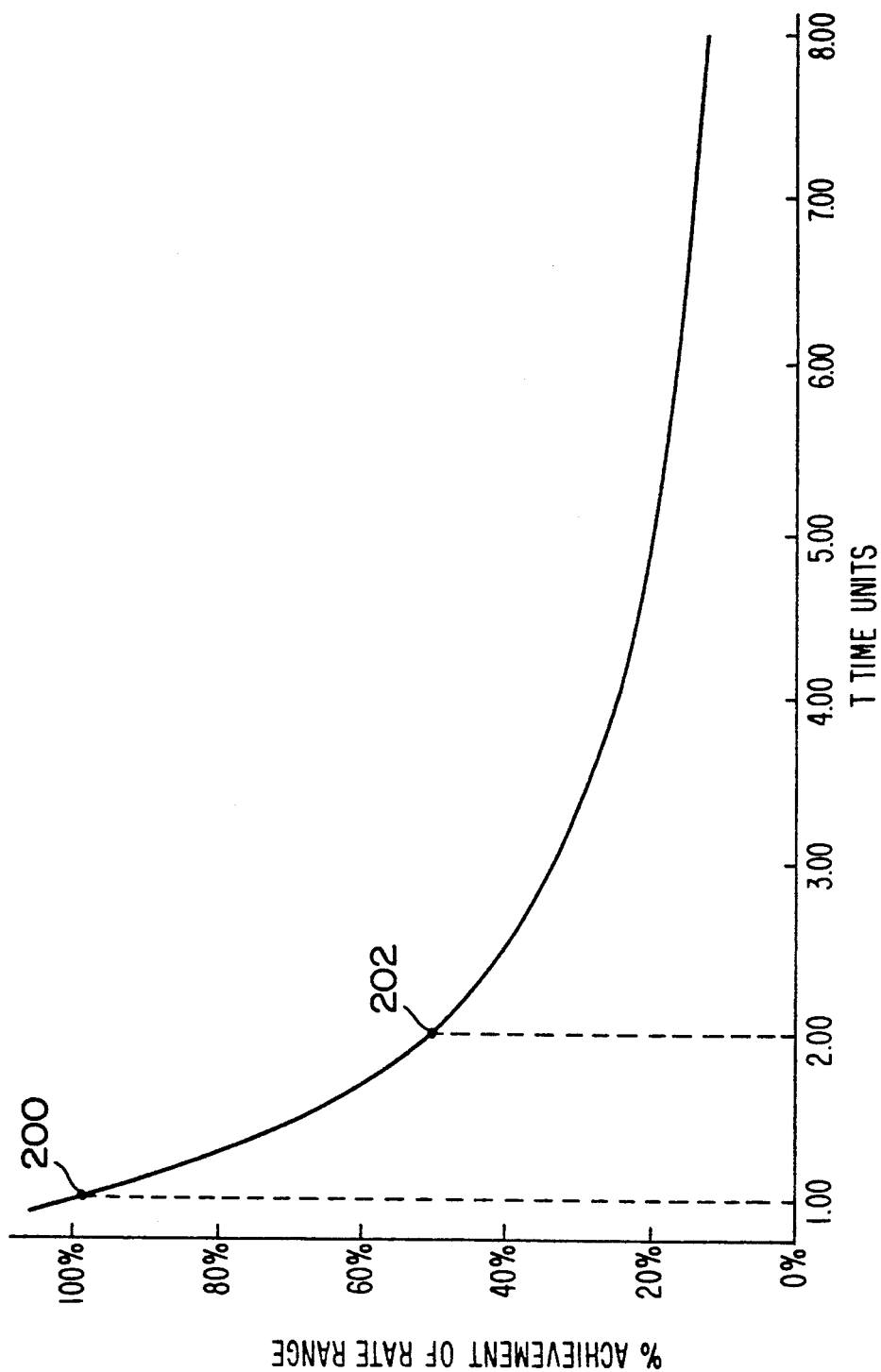
FIG. 6 is a graph illustrating combinations of Target Rate and time which will satisfy the Achievement Criteria for the pacemaker of FIG. 5.

Specification of the Achievement Criteria is one area of distinction between the Bennett et al. reference and a pacemaker in accordance with the present invention. Whereas in the Bennett et al. reference the Achievement Criteria are specified in terms of a single Achievement Rate value (e.g., 125-PPM) and a single Achievement Duration value (e.g., four seconds), a pacemaker in accordance with the presently disclosed embodiment of the invention instead recognizes a family of Achievement Rate/Achievement Duration pairs. In particular, with reference to FIG. 6, a Work Duration Identity curve describing the normalized Achievement Criteria for the presently disclosed embodiment of the present invention is shown. In FIG. 6, the horizontal axis represents time units, and the vertical axis represents percentage achievement of the rate range.

The curve shown in FIG. 6 defines the relationship between equivalent Target Time Units, with all points along the curve of FIG. 6 corresponding to equal Target Rate—Target Time Unit products. For example, the point designated 200 along the curve of FIG. 6 corresponds to a Target Time Unit of one time unit and a Target Rate that is at 100% of Achievement Range, where the Achievement Range is some range of pacing rates between the programmed Upper and Lower Rates. The point designated 202 along the curve of FIG. 6 corresponds to a Target Time Unit of two time units at a Target Rate that is at 50% of the Achievement. The points 200 and 202 have equivalent Target Rate—Target Time Unit products; indeed, all points along the curve of FIG. 6 have equivalent Target Rate—Target Time Unit products.

The Achievement Range is normalized so that it may correspond to any range of rates. However, in the presently preferred embodiment of the invention, 100% of Achievement Range is selected to correspond to the programmed Upper Rate. 0% of the Achievement Range may be selected to be at or above the programmed Lower Rate.

As an example of a specific application of the Work Duration Identity curve of FIG. 6, assume that pacemaker 10 is programmed with an Upper Rate of UR=150-PPM and a Lower Rate of LR=50-PPM. The Rate Response Range is thus 150-PPM minus 50-PPM equals 100-PPM. The Achievement Range may therefore be specified any range within the UR and the LR. As previously noted, the highest (100%) rate in the Achievement Range is preferably chosen to be the programmed UR, in this case 150-PPM. The lowest (0%) rate in the Achievement Range may be selected to be any rate between 50-PPM and 150-PPM. Assume, for the sake of illustration, that the lowest rate in the Achievement Range is selected to be 50-PPM, so that the Rate Range and the Achievement Range are coextensive, each spanning the 100-PPM range from 50-PPM to 150-PPM. Also assume that the time unit for the horizontal axis is selected to be one minute. Then, from FIG. 6, it can be seen that the Achievement Criteria is deemed to be met when the Target Rate is at 100% of the Rate Range (i.e., 150-PPM, computed as 100% of 100-PPM (equals 100-PPM) plus 50-PPM (the starting point of the Rate Range) for one time unit (i.e., one minute); or when the Target Rate is at 75% of the Rate Range (i.e., 125-PPM, computed as 75% of 100-PPM (equals 75-PPM) plus 50-PPM (the starting point of the Rate Range)) for 1.3 time units (i.e., 1.3-minutes); or when the Target Rate is at 50% of the Rate Range (i.e., 100-PPM, computed as 50% of 100-PPM (equals 50-PPM) plus 50-PPM (the starting point of the Rate Range)) for two time units (i.e., two minutes). These computations are summarized in the following Table 1:

TABLE 1

| PERCENT OF ACHIEVEMENT RANGE | PERCENT OF RATE RANGE | CORRESPONDS TO A TARGET RATE OF | TIME AT TARGET RATE TO MEET ACHIEVEMENT CRITERIA |
|---|---|---|---|
| 100% | 100% | 150-PPM | 1 TIME UNIT |
| 75% | 75% | 125-PPM | 1.3 TIME UNITS |
| 50% | 50% | 100-PPM | 2 TIME UNITS |
| 25% | 25% | 75-PPM | 4 TIME UNITS |
| 0% | 0% | 50-PPM | N/P |

Note that for 0% of Achievement Range, the entry in the "Time at Target Rate to Meet Achievement Criteria" column of Table 1 is "N/P" (Not Possible), since the Achievement Criteria cannot be met if the Target Rate stays at 0% of the Rate Range (50-PPM).

It is to be understood that the example discussed above and summarized in Table 1 is but one possible combination of parameters which may be selected for pacemaker 10 in accordance with the present invention. A second possible combination would be, for example, (again assuming a programmed UR of 150-PPM and a programmed LR of 50-PPM), an Achievement Range of 60-PPM, spanning from 90-PPM to 150-PPM. In this case, the Achievement Criteria would be met by a Target Rate at 100% of the Rate Range (i.e., 150-PPM, as before) for one time unit (again, assume one time unit equals one minute); or by a Target Rate at 85% of the Rate Range (i.e., 135-PPM, computed as 85% of 100-PPM (equals 85-PPM) plus 50-PPM (the starting point of the Rate Range) for 1.3 time units); or by a Target Rate at 70% of the Rate Range (i.e., 120-PPM, computed as 70% of 100-PPM (equals 70-PPM) plus 50-PPM (the starting point of the Rate Range) for two time units), and so on. The Achievement Criteria computations for this second example are summarized in the following Table 2:

TABLE 2

| PERCENT OF ACHIEVEMENT RANGE | PERCENT OF RATE RANGE | CORRESPONDS TO A TARGET RATE OF | TIME AT TARGET RATE TO MEET ACHIEVEMENT CRITERIA |
|---|---|---|---|
| 100% | 100% | 150-PPM | 1 TIME UNIT |
| 75% | 85% | 135-PPM | 1.3 TIME UNITS |
| 50% | 70% | 120-PPM | 2 TIME UNITS |
| 25% | 55% | 105-PPM | 4 TIME UNITS |
| 0% | 40% | 90-PPM | N/P |

As from Table 1, from Table 2, it is apparent that the Achievement Criteria in this second illustrative example cannot be met unless the Target Rate exceeds the lowest Achievement Range rate of 90-PPM.

A third illustrative example of a combination of parameters that may be selected for a pacemaker 10 in accordance with the presently disclosed embodiment of the invention is summarized in the following Table 3. In this third example, an Achievement Range of 40-PPM, spanning from 110-PPM to 150-PPM is selected.

TABLE 3

| PERCENT OF ACHIEVEMENT RANGE | PERCENT OF RATE RANGE | CORRESPONDS TO A TARGET RATE OF | TIME AT TARGET RATE TO MEET ACHIEVEMENT CRITERIA |
|---|---|---|---|
| 100% | 100% | 150-PPM | 1 TIME UNIT |
| 75% | 90% | 140-PPM | 1.3 TIME UNITS |
| 50% | 80% | 130-PPM | 2 TIME UNITS |
| 25% | 70% | 120-PPM | 4 TIME UNITS |
| 0% | 60% | 110-PPM | N/P |

In the above examples, the normalized time unit was assumed to be one minute; however, different values may be chosen, for example one and a third minutes, two minutes, four minutes, and so on. The 1/x nature of the Work Identity Curve of FIG. 6 provides clean, intuitive values for the Achievement Criteria, so that, for example, if time units of two minutes instead of one minute were specified, the values in the fourth column of each of Tables 1, 2, and 3 above would be doubled.

Having defined the Achievement Criteria as described above with reference to FIG. 6 and to Tables 1, 2, and 3, it remains to be shown how pacemaker 10 responds when the Achievement Criteria are met. In accordance with the presently disclosed embodiment of the invention, the decay curve modification performed by pacemaker 10 is defined in terms of several rate deceleration phases, specifically an Initial Deceleration Phase, an intermediate Modified Deceleration Phase, and a final Latent Deceleration Phase. In accordance with the presently disclosed embodiment of the invention, it is the intermediate Modified Deceleration Phase which is work-modulated, as shall be hereinafter described in some detail. By "work-modulated", it is meant that the duration of the Modified Deceleration Phase is a function of the amount of work recently performed by the patient, where the amount of work performed by the patient is measured by the output of the activity sensor.

Figure 7:
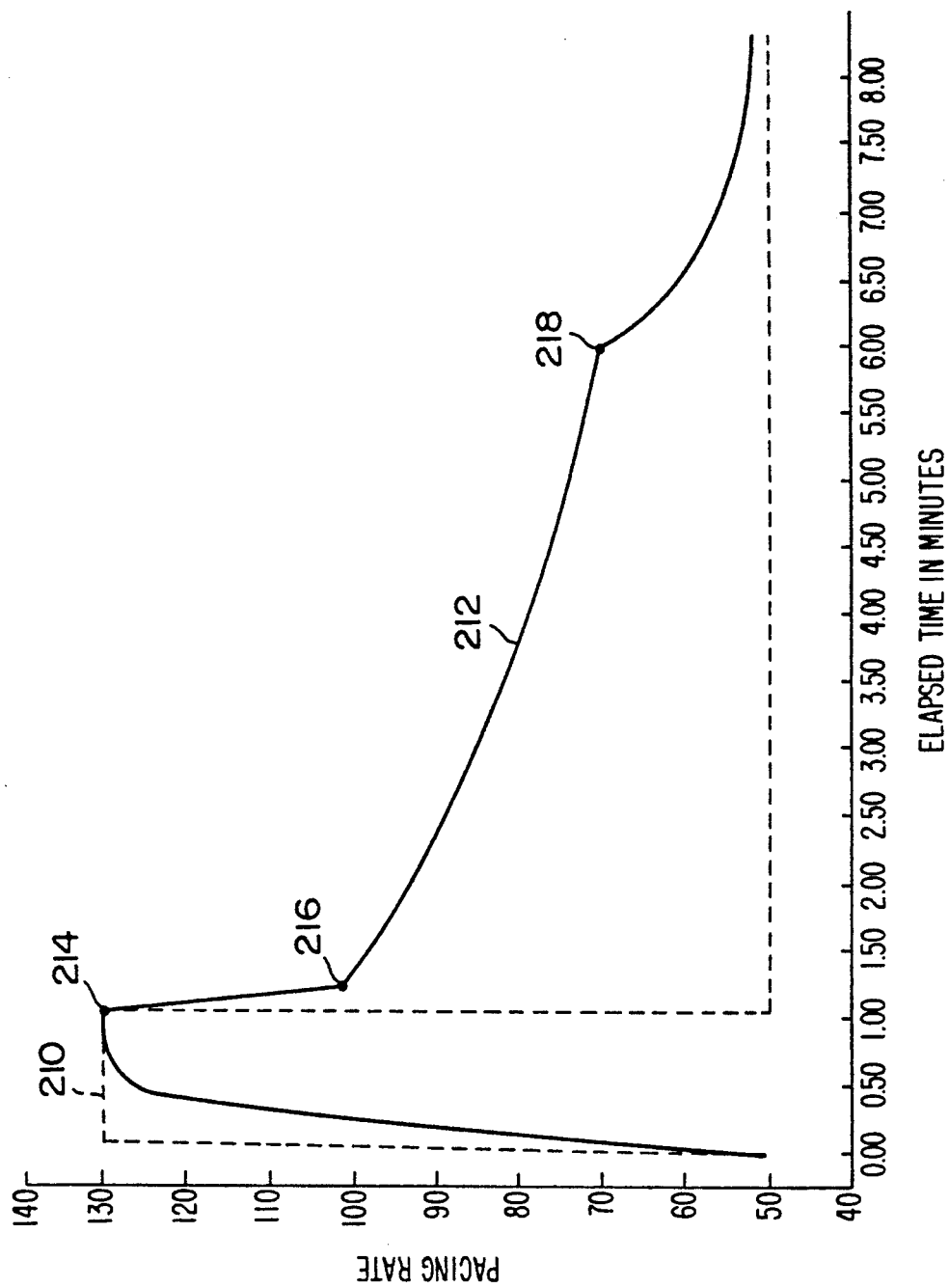
FIG. 7 is a graph of pacing rate versus time and Target Rate versus time showing the pacing rate response to patient activity of the pacemaker of FIG. 5.

FIG. 7 shows a solid line 212 corresponding to the pacing rate curve for pacemaker 10 in accordance with the presently disclosed embodiment of the invention. Also shown in FIG. 7 is a dashed line 210 representing the rate-responsive Target Rate function, computed by pacemaker 10 as described in the Bennett et al. and Sivula et al. references. Pacing rate curve 212 represents the actual pacing rate of pacemaker 10, derived from the Target Rate as subjected to the Activity Response Time Acceleration function and the Activity Rate Gain Function, described in the foregoing definitions of terms, and the Activity Response Deceleration function of the present invention.

In FIG. 7, the Target Rate increases from 50-PPM (the programmed LR) to 130-PPM (the programmed UR) at time T=0. The actual pacing rate function 212, of course, does not make an immediate transition in response to the abrupt change in Target Rate, but instead gradually increases from 50-PPM to 130-PPM as mandated by the Acceleration function. As previously noted, the programmed Acceleration Time Constant defines how long it will take to achieve an acceleration from the present pacing rate to 90% of the Target Rate. In the presently disclosed embodiment of the invention, the clinician can select, by means of the external programmer, one of three different Acceleration Time Constants, 15-Sec, 30-Sec, or 1-min.

At time T=1-min, the Target Rate computed by pacemaker 10 falls from 130-PPM to 50-PPM. The deceleration of the actual pacing rate is determined in accordance with the work-modulated decay rate function of the presently disclosed embodiment of the invention. Work-modulated deceleration is intended to provide a more physiologic pacing rate deceleration once a patient terminates exercise at a higher heart rate. The Initial Deceleration Phase occurs immediately after a period of intense exercise, followed by the intermediate Work-Modulated Deceleration Phase.

In FIG. 7, the Initial Deceleration Phase begins at deflection point 214, and continues to deflection point 216. The Initial Deceleration Phase has a 2.5-min Deceleration Time Constant in the presently preferred embodiment.

In the Bennett et al. device, the physician selects an Upper Switch Rate and a Lower Switch Rate, as previously described with reference to FIG. 3. For the work-modulated pacing rate deceleration function of the present invention, the physician selects only a single Switch Rate, generally corresponding to the Upper Switch Rate of the Bennet et al. reference. In the example illustrated in FIG. 7, it is assumed that the Switch Rate is programmed to a value of approximately 100-PPM. In FIG. 7, the pacing rate curve 212 reaches the Switch Rate at point 216. In FIG. 7, the Target Rate curve 210 is shown to be at 100% of the Rate Range for one minute. Thus, at time T=1-min, the Achievement Criteria defined by the Work Identity Curve of FIG. 6 are satisfied (Achievement Duration of 1-min and Achievement Rate of 100% of the Target Rate Range corresponds to point 200 on the Work Identity Curve). Since the Achievement Criteria are satisfied, the work-modulated rate deceleration function will be enabled, so that at the Switch Rate, the programmed Deceleration Time Constant will be temporarily replaced with a Work-Modulated Deceleration Time Constant selected by the physician.

As noted above, in the presently preferred embodiment of the invention the Programmed Switch Rate is defined and implemented as is the Upper Switch Rate in the Bennett et al. device, namely as a selected percentage of the difference between the programmed LR and UR. However, it is also contemplated by the inventors that the Programmable Switch Rate could be defined and implemented as a function of the current work value. In particular, it is contemplated by the inventors that the Programmable Switch Rate could be increased in proportion to increases in the current Work value, as in the following equation:

$$\text{Switch Rate} = f(\text{Work}) = (\text{Work}/X) \times (\text{Upper Rate} - \text{Lower Rate}) + \text{Lower Rate}$$

where X is a programmable or predetermined constant.

In the disclosed embodiment, the Work-Modulated Deceleration Time Constant is 20-min. Thus, beginning at point 216 in FIG. 7, the pacing rate will begin to decelerate along a 20-min deceleration curve.

In the Bennett et al. device, the pacing rate decays according to the modified deceleration time constant until the pacing rate reaches the Lower Switch Rate; that is, the modified decay curve terminates when the pacing rate reaches the Lower Switch Rate. In the presently disclosed embodiment of the invention, on the other hand, the termination of the Intermediate Deceleration Phase is not determined according to the pacing rate, but is instead determined by the amount of work recently performed by the patient.

Pacemaker 10 in accordance with the presently disclosed embodiment of the invention defines "work" as the difference between the Target Rate and a preselected Rest Rate over time, where the Rest Rate is defined as follows:

$$\text{Rest Rate} = \text{Lower Rate} + 0.1 \times (\text{Upper Rate} - \text{Lower Rate})$$

When the Work-Modulated Rate Response Deceleration Function is enabled, the pacemaker maintains a running Work value that is updated every two seconds in much the same way as the Target Rate is computed every two seconds. The Work value is computed every two seconds according to the following recursive formula:

If (Target Rate ≧ Pacing Rate), then $$\text{Work}_N = \text{Work}_{N-1} + (\text{Target Rate} - \text{Rest Rate});$$

If (Target Rate ≧ Pacing Rate), then $$\text{Work}_N = \text{Work}_{N-1} - \text{Work Decrement Value}$$

where $\text{Work}_N$ is the Work value for the current two-second interval, $\text{Work}_{N-1}$ is the Work value from the previous two-second interval, and Work Decrement Value is a value corresponding to the amount to subtract from the Work value when the current pacing rate exceeds the current Target Rate. The Work Decrement Value may be a programmable value; however, in the presently preferred embodiment of the invention, the Work Decrement Value is defined as (Maximum Exercise Value/20).

An upper limit on the Work value may be imposed, either as a programmable function, or as a built-in function. To this end, a Maximum Exercise Time value, which may either be programmably selectable by the physician or preset at the time of manufacture, is defined. In each two second interval, if the new Work value exceeds the Maximum Exercise Time value, the Work value is forced to the Maximum Exercise Time.

It is to be noted that in defining Work in the manner set forth above, selection of the Rest Rate is equivalent to selecting the Achievement Range to extend from a lower bound of (Lower Rate+(0.1×(Upper Rate−Lower Rate))) to an upper bound of UR.

With Work defined in this manner, for constant work by the patient a larger Work Decrement Value (or Smaller Maximum Exercise Time) will shorten the duration of the Work-Modulated portion of the rate deceleration function.

The rate deceleration of pacemaker 10 is subjected to the Work-Modulated Deceleration function whenever the current Work value is greater than zero; otherwise, the programmed Deceleration Time Constant controls rate deceleration.

While the pacing rate is greater than the programmed Switch Rate, the programmed Deceleration Time Constant will be used in calculating the pacing rate. When the pacing rate decelerates to the Switch Rate, a Modified Deceleration Time Constant of 20-min is used. The Modified Deceleration Time Constant controls the pacing rate deceleration until the Work value reaches zero, at which time the rate deceleration will be governed either by the original, programmed Deceleration Time Constant, or by another programmed deceleration value (although in the preferred embodiment, the programmed Deceleration Time Constant is used).

Figure 8:
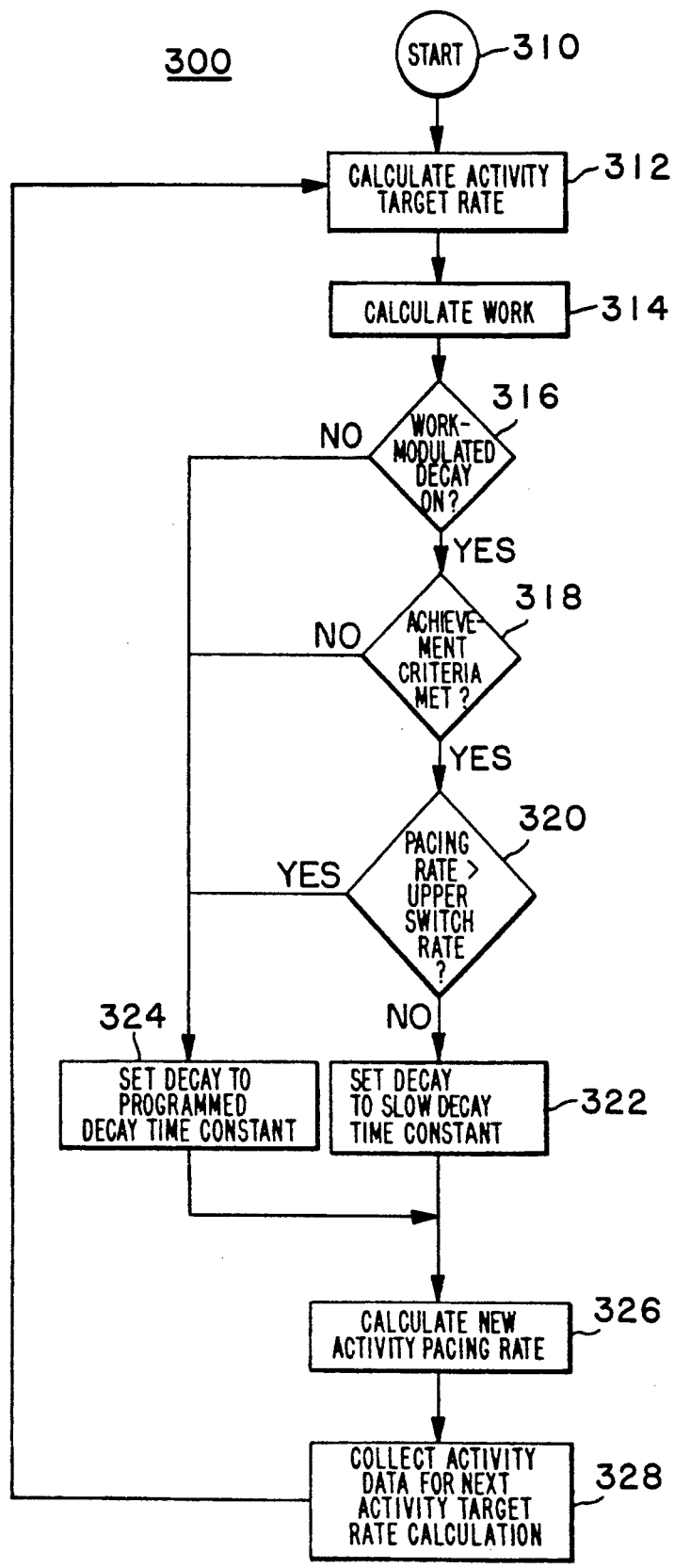
FIG. 8 is a flow diagram depicting the operation of the pacemaker of FIG. 5.

In FIG. 8, a flow diagram 300 illustrating the operation of the Work-Modulated Pacing Rate Deceleration function in accordance with the presently disclosed embodiment of the invention is shown. Pacemaker 10 starts at 310, and then determines, at 312, a new rate-response Target Rate according to the Target Rate equation set forth above with reference to FIG. 4.

At 314, the Work value is calculated according to the formula set forth above. At 316, pacemaker 10 determines whether the Work-Modulated Pacing Rate Deceleration Function has been enabled, such as by an external programmer or the like. If the Work-Modulated Deceleration Function has not been enabled, pacemaker 10 sets the deceleration time constant to the programmed value, at block 324. Pacemaker 10 then calculates a new pacing rate based upon the current pacing rate, Target Rate, and Deceleration or Acceleration Time Constants, at 326, and saves the activity-related data at 328 for use in calculating the new Target Rate during the next two-second interval. The above routine is repeated until the Work-Modulated Rate Deceleration Function is enabled.

If the Work-Modulated Rate Deceleration Function is found to be enabled at decision block 316, pacemaker 10 then determines whether the Achievement Criteria have been met. In the presently disclosed embodiment of the invention, this determination is made by determining whether the current Work value is greater than zero. If Work is greater than zero at block 318, pacemaker 10 determines whether the current Pacing Rate is greater than the programmed Switch Rate. If so, the programmed Deceleration Time Constant is used (block 324); if not the Work-Modulated Deceleration Time Constant is used (block 322).

Then, pacemaker 10 computes the new pacing rate, based upon the current pacing rate, Target Rate, and Acceleration or Deceleration Time Constants, at block 326. Activity sensor data is accumulated at block 328, and the process is repeated beginning with block 312.

Figure 9:
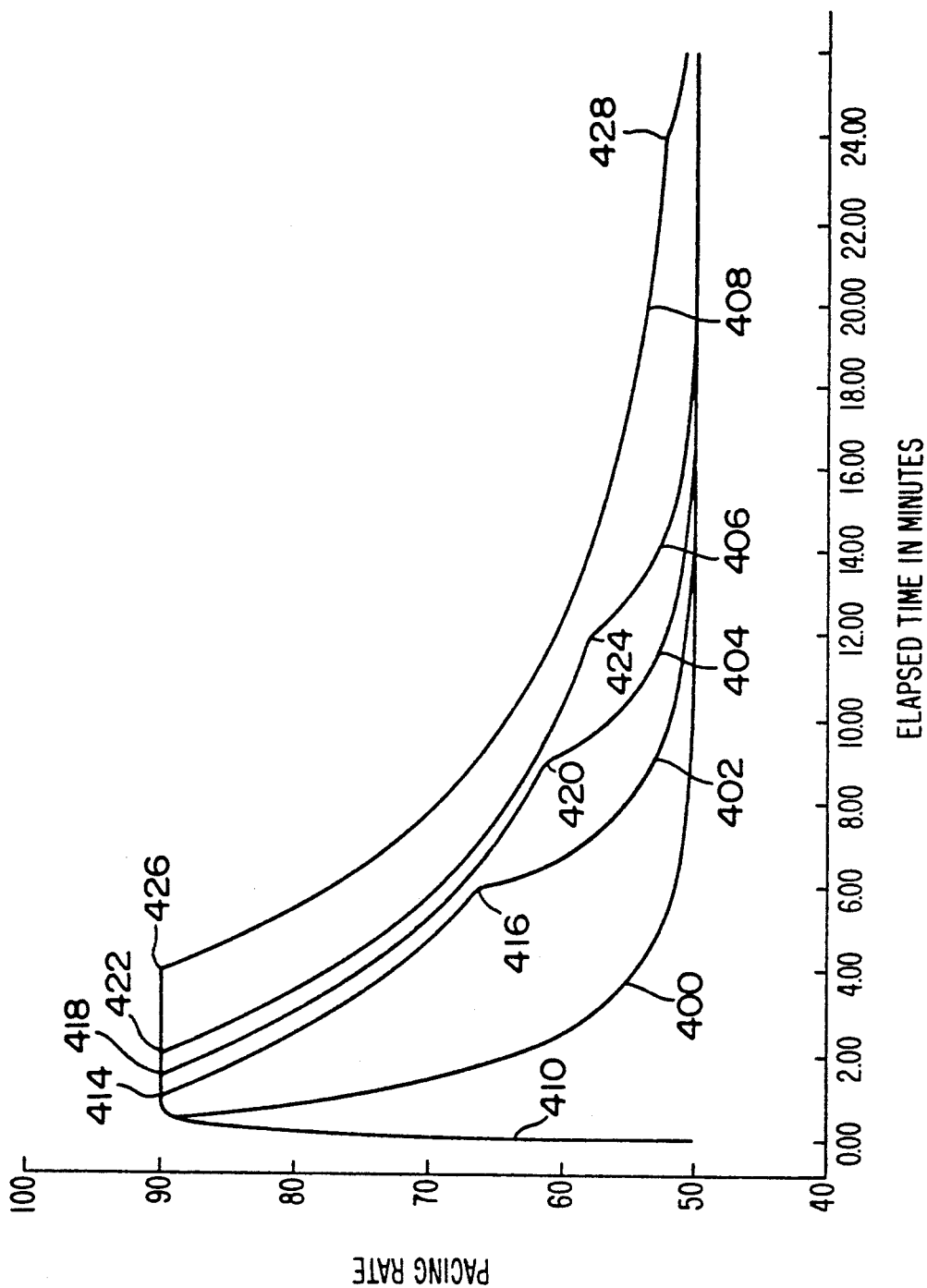
FIG. 9 is a graph of pacing rate versus time showing several different pacing rate responses to patient activity of the pacemaker of FIG. 5.

To further illustrate the effect of the Work-Modulated Deceleration Function on the pacing rate, several pacing rate curves are shown in FIG. 9. In FIG. 9, five pacing rate curves designated 400, 402, 404, 406, and 408 are shown. Each of the pacing rate curves share an identical acceleration phase, designated in FIG. 9 as 410, but differ from one another in the amount of time each one spends at a maximum pacing rate of approximately 90-PPM. In the case of curve 400, the length of time in which the Target Rate exceeds the pacing rate is so short that very little Work is accumulated; as a result, the deceleration phase of curve 400 is largely controlled by the programmed Deceleration Time Constant. For curve 402, however, the pacing rate remains at 90-PPM for a longer period of time, allowing the Work value to increase more.

In FIG. 9, it is assumed that the Switch Rate is programmed to some value above 90-PPM, so that none of the curves shown in FIG. 9 will undergo an initial Rapid Deceleration Phase at the programmed Deceleration Time Constant. For curve 402, when the Target Rate falls substantially at point 414, the rate deceleration will be governed by the Work-Modulated Deceleration function, since the Work value at point 414 is greater than zero. Specifically, the Work-Modulated Deceleration Time Constant (e.g., 20-min) will govern the deceleration from point 414 to point 416. During the time between points 414 and 416, the Work Value will decay as described in the Work value formula set forth hereinabove. At point 416, the Work value has decayed to zero, so that the deceleration of the pacing rate is then governed by the programmed Deceleration Time Constant of 2.5-min. This deceleration occurs until the pacing rate has returned to the programmed LR.

For curve 404, the pacing rate accelerates from 50-PPM to 90-PPM at the same time as curves 400 and 402, but remains at the 90-PPM level for a longer period of time, until point 418, at which time it is assumed that the Target Rate drops to 50-PPM. Since curve 404 remained at the 90-PPM level for a longer time than curve 402, more Work is allowed to accumulate for curve 404 than for curve 402. Since more Work has accumulated, the Work-Modulated Deceleration phase of curve 404 lasts longer than for curve 402. As can be seen from FIG. 9, the Work-Modulated Deceleration phase for curve 404 lasts from point 418 to point 420, when the programmed Deceleration Time Constant is engaged.

Similarly, curve 406 undergoes an acceleration phase identical to that for curves 400, 402 and 404, but remains at the 90-PPM level for a longer time, until point 422. Since more Work accumulates for curve 406 than for any of the curves 400, 402 or 404, the Work-Modulated Deceleration phase for curve 406 lasts longer than for those curves, from point 422 to point 424. At point 424, deceleration resumes with the programmed Deceleration Time Constant.

Finally, curve 408 undergoes the same acceleration phase as curves 400, 402, 404, and 406, but remains at the 90-PPM level for considerably longer, until point 426, allowing proportionally more work to accumulate. When the Target Rate returns to 50-PPM at point 426, the Work-Modulated Deceleration Phase begins, lasting until the Work value was decayed to zero at point 428. Thereafter, deceleration of curve 408 occurs at the programmed Deceleration Time Constant.

Figure 10:
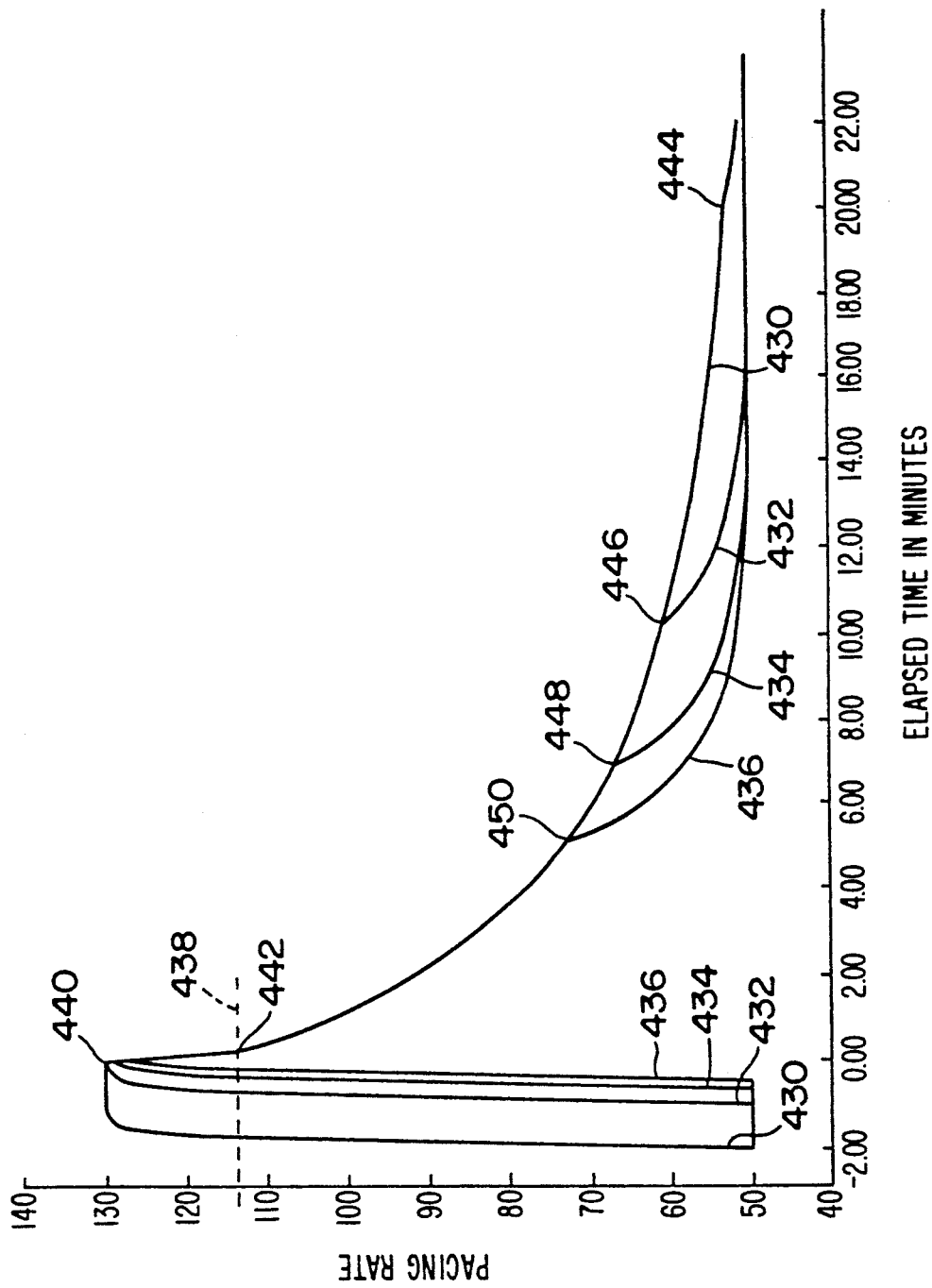
FIG. 10 is a graph of pacing rate versus time showing several different pacing rate responses to patient activity of the pacemaker of FIG. 5.

Turning now to FIG. 10, another group of pacing rate curves is depicted. In FIG. 10, pacing rate curves 430, 432, 434, and 436 are shown, with each curve undergoing an identical acceleration phase from 50-PPM to 130-PPM. In FIG. 10, however, the acceleration phases of the four curves begin at different times, whereas in FIG. 9, the acceleration phases of the curves began at the same time (T=0). In FIG. 10, the deceleration phases begin at the same time (T=0), whereas in FIG. 9 the deceleration phases began at different times. In FIG. 10, the programmed Switch Rate of approximately 112-PPM is indicated by dashed line 438.

FIG. 10 illustrates the relationship between the deceleration curves resulting from the pacemaker's response to varying amounts of accumulated Work. Since each of the rate curves of FIG. 10 begins its deceleration phase from a pacing rate above the programmed Switch Rate 438, the deceleration phases of each curve each begin with a rapid Initial Deceleration Phase at the programmed Deceleration Time Constant of 5-min., until the respective pacing rates have been reduced to the Switch Rate. Since the Initial Deceleration Phase is, in accordance with the presently disclosed embodiment of the invention, not work-modulated, the duration of the Initial Deceleration Phase for each of the curves in FIG. 10 is the same, lasting from point 440 to point 442.

Curve 430, which prior to time T=0 remains at the upper rate of 130-PPM for the longest time of any of the curves of FIG. 10, has a Work-Modulated Deceleration Phase that begins at point 442 and lasts until point 444 (time T=20-min.) Curve 432, which remains at the 130-PPM level for a shorter period of time, also has a Work-Modulated Deceleration Phase that begins at point 442; however, for curve 432, the Work-Modulated Deceleration Phase only lasts until point 446, since less Work accumulated during the shorter time that curve 432 remained at the 130-PPM level. Similarly, the Work-Modulated Deceleration Phase of curve 434 extends only from point 442 to point 448, and that of curve 436 from point 442 to point 450.

FIG. 10 emphasizes the fact that the time constant governing the Initial Deceleration Phase of different rate curves is the same, regardless of how much Work has accumulated for the different rate curves; likewise, the time constant governing the Work-Modulated Deceleration Phase of different rate curves is the same, regardless of accumulated Work. It is the duration of the Work-Modulated Deceleration Phase that varies in accordance with accumulated Work.

From the foregoing detailed description of a specific embodiment of the present invention, it should be apparent that a pacemaker having a Work-Modulated Pacing Rate Deceleration function has been disclosed which more closely mimics the natural physiologic response of a human heart to increases and decreases in patient activity.

Although a specific embodiment of the invention has been set forth herein in some detail, it is to be understood that this has been done for the purposes of illustration only, and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A method of operating a rate-responsive cardiac pacemaker, wherein said pacemaker is responsive to a change in a patient's level of activity to vary a pacing delivery rate, comprising the steps of:
   (a) detecting when said patient's level of activity over time exceeds a predetermined level;
   (b) quantifying said excess of detected patient level of activity;
   (c) associating at least one work value with said quantification;
   (d) increasing the pacing delivery rate in response to said work value;
   (e) detecting when said patient's level of activity returns to said predetermined level; and
   (f) decreasing the pacing delivery rate along a deceleration curve that is modulated according to said at least one work value.

2. A rate responsive cardiac pacemaker comprising:
   an activity sensor producing an activity signal indicative of detected levels of a patient's activity;
   processing means, coupled to the activity sensor, responsive to said activity signal to compute a pacing rate and a work value, said work value comprising a quantification of the patient's activity over time;
   a pulse generator, coupled to said processing means, for producing stimulating pulses at said computed pacing rate;
   a pacing lead means, coupled to said pulse generator, for delivering said stimulating pulses to a patient's heart; and
   means for modulating deceleration of said pacing rate according to said work value.

3. An implantable, rate-responsive cardiac pacemaker, comprising:
   a pulse generator, for generating cardiac stimulating pulses;
   a pacing lead, coupled to said pulse generator and adapted to convey said stimulating pulses to a patient's heart;
   a piezoelectric activity sensor, adapted to be coupled to a patient and responsive to patient motion to produce an activity signal;
   an activity circuit, coupled to said activity sensor and said pulse generator, and responsive to said activity signal to produce a stream of activity pulses;
   an activity pulse counting circuit, coupled to said activity circuit and adapted to periodically compute an activity count value corresponding to a number of activity pulses produced by said activity circuit during a predetermined time interval;
   a target rate computing circuit, coupled to said counting circuit and adapted to periodically compute a target pacing rate value proportional to said activity count value;
   a work computing circuit, coupled to said rate computing circuit and adapted to periodically compute a work value that is proportional to excesses of previously computed target pacing rate values over a predetermined threshold value; and
   a pacing rate computing circuit, coupled to said target rate computing circuit and to said work computing circuit, and adapted to periodically derive a pacing rate value from said target rate value and said work value;
   wherein said pacing rate computing circuit is adapted to vary a rate of decrease in said pacing rate value in an inversely proportional relationship to said work value.

4. A method of controlling a pacing rate of a cardiac pacemaker comprising the steps of:
  (a) setting said pacing rate to an initial rate;
  (b) increasing said pacing rate from said initial rate to a first target rate along a predetermined acceleration curve;
  (c) associating a work value with said increase in pacing rate; and
  (d) decreasing said pacing rate from said first target rate along a deceleration curve having a plurality of phases with different deceleration rates, at least one of said plurality of phases having a duration modulated by said work value.

5. The method of claim 4, wherein the step of associating includes associating the work value such that said work value is proportional to a time interval during which said first target rate exceeds a predetermined rest rate, and proportional to a margin between said pacing rate and said predetermined rest rate during said time interval.

* * * * *

UNITED STATES PATENT AND TRADEMARK OFFICE
CERTIFICATE OF CORRECTION

PATENT NO. : 5,312,453
DATED : May 17, 1994
INVENTOR(S) : Michael B. Shelton, et al It is certified that error appears in the above-indentified patent and that said Letters Patent is hereby corrected as shown below:

Column 20, Line 51, delete "Target Rate $\geq$ Pacing Rate" and insert in its place --Target Rate $<$ Pacing Rate--.

Signed and Sealed this

Sixth Day of September, 1994

Attest:

BRUCE LEHMAN

*Attesting Officer*  *Commissioner of Patents and Trademarks*